US007527053B2

(12) United States Patent
DeVries et al.

(10) Patent No.: US 7,527,053 B2
(45) Date of Patent: May 5, 2009

(54) METHOD AND APPARATUS FOR ATTENUATING COMPRESSOR NOISE

(75) Inventors: Douglas F. DeVries, Kenmore, WA (US); Malcolm R. Williams, San Clemente, CA (US)

(73) Assignee: Cardinal Health 203, Inc., Wilmington, DE (US)

( * ) Notice: Subject to any disclaimer, the term of this patent is extended or adjusted under 35 U.S.C. 154(b) by 325 days.

(21) Appl. No.: 11/088,316

(22) Filed: Mar. 23, 2005

(65) Prior Publication Data
US 2005/0166921 A1 Aug. 4, 2005

Related U.S. Application Data

(63) Continuation-in-part of application No. 10/912,747, filed on Aug. 4, 2004, now Pat. No. 7,188,621.

(60) Provisional application No. 60/492,421, filed on Aug. 4, 2003.

(51) Int. Cl.
*A61M 16/00* (2006.01)
(52) U.S. Cl. ............................. 128/204.21; 128/204.18
(58) Field of Classification Search ............ 128/200.24, 128/204.18, 204.21, 204.28, 205.11, 205.13, 128/205.14, 205.15, 205.16, 205.17; 181/272, 181/273, 282, 256, 266
See application file for complete search history.

(56) References Cited

U.S. PATENT DOCUMENTS 56,614 A 7/1866 Roots et al.

(Continued)

FOREIGN PATENT DOCUMENTS

DE 3238015 4/1984

(Continued)

OTHER PUBLICATIONS

M.L. Munjal, "Acoustics of Ducts and Mufflers," John Wiley & Sons, 1987, chapter 8.

(Continued)

*Primary Examiner*—Justine R Yu
*Assistant Examiner*—Annette F Dixon
(74) *Attorney, Agent, or Firm*—Baker Hostetler LLP

(57) ABSTRACT

The invention comprises a method and apparatus for reducing the noise generated by compressors, including Roots-type blowers. The invention has particular use for reducing noise generated by compressors used in mechanical ventilators, though the advantages thereof may be realized in many different applications. One embodiment of the invention comprises a noise-attenuating gas flow path for a compressor contained in a portable ventilator housing. In one embodiment, the gas flow path comprises a plurality of chambers interconnected by flow tubes. The flow path is folded so as to fit into the limited space of a portable ventilator housing. The dimensions of the chambers and the flow tubes are selected so that an impedance mismatch is created between the chambers and the flow tubes. In one embodiment of the invention, the flow path comprises one or more perforated tubes located in one or more of the chambers. The perforated tube has a port through which gas is accepted and at least one exterior tube through which gas exits. Impedance mismatches are created between the inlet chamber and the exterior tubes and between the exterior tubes and the chamber in which the perforated tube is located, which are useful in attenuating noise. One embodiment of the invention comprises a noise attenuating mounting system for a compressor. The mounting system comprises flexible mounts that cooperate to dampen vibrations generated by the compressor.

26 Claims, 5 Drawing Sheets

U.S. PATENT DOCUMENTS

| | | | |
|---|---|---|---|
| 587,907 A | 8/1897 | Ames et al. | |
| 1,769,153 A | 7/1930 | Meyer | |
| 2,014,932 A | 9/1935 | Hallett | 230/141 |
| 2,787,999 A | 4/1957 | Bennett | 128/30 |
| 3,089,638 A | 5/1963 | Rose | 230/141 |
| 3,094,274 A | 6/1963 | Thompson | 230/224 |
| 3,371,856 A | 3/1968 | Thelen et al. | 230/141 |
| 3,459,395 A | 8/1969 | Scotto | |
| 3,658,443 A | 4/1972 | Fumagalli | 417/394 |
| 3,941,206 A * | 3/1976 | Halter | 181/256 |
| 4,080,103 A | 3/1978 | Bird | 417/3 |
| 4,121,578 A | 10/1978 | Torzala | 128/142 R |
| 4,215,977 A | 8/1980 | Weatherston | 418/1 |
| 4,220,219 A | 9/1980 | Flugger | 181/265 |
| 4,227,869 A | 10/1980 | Eriksson | 418/206 |
| 4,239,039 A | 12/1980 | Thompson | 128/205.24 |
| 4,267,899 A * | 5/1981 | Wagner et al. | 181/272 |
| 4,323,064 A | 4/1982 | Hoenig et al. | 128/204.21 |
| 4,448,192 A | 5/1984 | Stawitcke et al. | 128/204.26 |
| 4,455,132 A | 6/1984 | Messori | 418/206 |
| 4,495,947 A | 1/1985 | Motycha | 128/205.14 |
| 4,564,345 A | 1/1986 | Mueller | 418/206 |
| 4,595,349 A | 6/1986 | Preston et al. | 418/206 |
| 4,609,335 A | 9/1986 | Uthoff, Jr. | 418/201 |
| 4,666,384 A | 5/1987 | Kaga et al. | 418/150 |
| 4,673,058 A | 6/1987 | Roberts et al. | 181/266 |
| 4,684,330 A | 8/1987 | Andersson et al. | 417/360 |
| 4,686,999 A | 8/1987 | Snyder et al. | 128/706 |
| 4,702,240 A | 10/1987 | Chaoui | 128/204.18 |
| 4,768,934 A | 9/1988 | Soeters, Jr. | 418/1 |
| 4,781,541 A | 11/1988 | Sohler et al. | 417/312 |
| 4,794,922 A | 1/1989 | DeVries | 128/204.18 |
| 4,844,044 A | 7/1989 | McGovern | 123/559.1 |
| 4,846,302 A | 7/1989 | Hetherington | 181/243 |
| 4,867,151 A | 9/1989 | Bird | 128/201.17 |
| 4,938,670 A | 7/1990 | Lee | 418/150 |
| 4,957,107 A | 9/1990 | Sipin | 128/204.21 |
| 4,975,032 A | 12/1990 | Arai et al. | 418/150 |
| 5,040,959 A | 8/1991 | Fukagawa | 418/150 |
| 5,056,995 A | 10/1991 | Tamura et al. | 418/201.1 |
| 5,131,829 A | 7/1992 | Hampton | 418/189 |
| 5,145,349 A | 9/1992 | McBurnett | 418/206 |
| 5,152,684 A | 10/1992 | Steffens | 418/150 |
| 5,161,525 A | 11/1992 | Kimm et al. | 128/204.26 |
| 5,211,170 A | 5/1993 | Press | 128/204.18 |
| 5,222,148 A | 6/1993 | Yuan | 381/71 |
| 5,237,987 A | 8/1993 | Anderson et al. | 128/204.18 |
| 5,239,994 A | 8/1993 | Atkins | 128/204.18 |
| 5,335,651 A | 8/1994 | Foster et al. | 128/202.13 |
| 5,350,888 A | 9/1994 | Sager, Jr. et al. | 181/247 |
| 5,398,676 A | 3/1995 | Press et al. | 128/204.23 |
| 5,439,358 A | 8/1995 | Weinbrecht | 418/15 |
| 5,452,714 A | 9/1995 | Anderson et al. | 128/205.11 |
| 5,542,416 A | 8/1996 | Chalvignac | 128/204.23 |
| 5,577,152 A | 11/1996 | Chen | 388/804 |
| 5,582,163 A | 12/1996 | Bonassa | 128/204.26 |
| 5,632,270 A | 5/1997 | O'Mahony et al. | 128/204.24 |
| 5,638,600 A | 6/1997 | Rao et al. | 29/888.02 |
| 5,664,563 A | 9/1997 | Schroeder et al. | 128/204.25 |
| 5,687,717 A | 11/1997 | Halpern et al. | 128/630 |
| 5,694,926 A | 12/1997 | DeVries et al. | 128/205.24 |
| 5,701,883 A | 12/1997 | Hete et al. | 128/204.26 |
| 5,702,240 A | 12/1997 | O'Neal et al. | 418/9 |
| 5,760,348 A * | 6/1998 | Heuser | 181/272 |
| 5,763,792 A | 6/1998 | Kullik | 73/861.53 |
| 5,783,782 A | 7/1998 | Sterrett et al. | 181/272 |
| 5,823,186 A | 10/1998 | Rossen et al. | 128/204.21 |
| 5,831,223 A | 11/1998 | Kesselring | 181/227 |
| 5,868,133 A | 2/1999 | DeVries et al. | 128/204.21 |
| 5,881,722 A | 3/1999 | DeVries et al. | 128/204.21 |
| 5,918,597 A | 7/1999 | Jones et al. | 128/205.18 |
| 5,931,159 A | 8/1999 | Suzuki et al. | 128/204.18 |
| 5,944,501 A | 8/1999 | Yokoi | 418/181 |
| 6,009,871 A | 1/2000 | Kiske et al. | 128/204.21 |
| 6,076,523 A | 6/2000 | Jones et al. | 128/205.11 |
| 6,099,277 A | 8/2000 | Patel et al. | 418/1 |
| 6,102,038 A | 8/2000 | DeVries | 128/205.24 |
| 6,125,844 A | 10/2000 | Samiotes | 128/200.23 |
| 6,152,129 A | 11/2000 | Berthon-Jones | 128/200.24 |
| 6,152,135 A | 11/2000 | DeVries et al. | 128/205.24 |
| 6,155,257 A | 12/2000 | Lurie et al. | 128/204.23 |
| 6,158,430 A | 12/2000 | Pfieffer et al. | 128/202.27 |
| 6,158,434 A | 12/2000 | Lugtigheid et al. | 128/204.22 |
| 6,164,412 A | 12/2000 | Allman | |
| 6,176,693 B1 | 1/2001 | Conti | 418/180 |
| 6,279,574 B1 | 8/2001 | Richardson et al. | 128/204.18 |
| 6,283,246 B1 * | 9/2001 | Nishikawa | 181/255 |
| 6,305,372 B1 | 10/2001 | Servidio | 128/204.21 |
| 6,354,558 B1 | 3/2002 | Li | |
| 6,412,483 B1 | 7/2002 | Jones et al. | 128/205.11 |
| 6,474,960 B1 | 11/2002 | Hansmann | 417/363 |
| 6,484,719 B1 | 11/2002 | Berthon-Jones | 128/204.23 |
| 6,526,970 B2 | 3/2003 | DeVries et al. | 128/204.21 |
| 6,543,449 B1 | 4/2003 | Woodring et al. | 128/204.18 |
| 6,558,137 B2 * | 5/2003 | Tomell et al. | 417/312 |
| 6,564,798 B1 | 5/2003 | Jalde | 128/205.24 |
| 6,571,792 B1 | 6/2003 | Hendrickson et al. | 128/203.12 |
| 6,571,796 B2 | 6/2003 | Banner et al. | 128/204.26 |
| 6,591,835 B1 | 7/2003 | Blanch | 128/204.25 |
| 6,615,831 B1 | 9/2003 | Tuitt et al. | 128/204.18 |
| 6,619,286 B2 | 9/2003 | Patel | 128/204.26 |
| 6,626,175 B2 | 9/2003 | Jafari et al. | 128/204.21 |
| 6,629,525 B2 | 10/2003 | Hill et al. | 128/202.26 |
| 6,629,531 B2 | 10/2003 | Gleason et al. | 128/205.25 |
| 6,629,934 B2 | 10/2003 | Mault et al. | 600/538 |
| 6,631,716 B1 | 10/2003 | Robinson et al. | 128/204.21 |
| 6,637,430 B1 | 10/2003 | Voges et al. | 128/200.14 |
| 6,651,658 B1 | 11/2003 | Hill et al. | 128/204.23 |
| 6,666,209 B2 | 12/2003 | Bennett et al. | 128/200.24 |
| 6,672,300 B1 | 1/2004 | Grant | 124/204.26 |
| 6,691,702 B2 | 2/2004 | Appel et al. | 128/202.26 |
| 6,691,707 B1 | 2/2004 | Gunaratnam et al. | 128/206.21 |
| 6,708,690 B1 | 3/2004 | Hete et al. | 128/204.18 |
| 6,745,770 B2 | 6/2004 | McAuliffe et al. | 128/205.24 |
| 6,752,240 B1 * | 6/2004 | Schlagenhaft | 181/249 |
| 6,764,534 B2 | 7/2004 | McCombs et al. | |
| 6,770,037 B2 | 8/2004 | Sullivan et al. | 600/529 |
| 6,782,888 B1 | 8/2004 | Friberg et al. | 128/204.18 |
| 6,802,225 B2 | 10/2004 | Shahar et al. | 73/861.52 |
| 6,820,618 B2 | 11/2004 | Banner et al. | 128/204.23 |
| 6,837,260 B1 | 1/2005 | Kuehn | 137/315.01 |
| 6,877,511 B2 | 4/2005 | DeVries et al. | 128/204.26 |
| 6,968,842 B1 | 11/2005 | Truschel et al. | 128/204.18 |
| 7,004,908 B2 | 2/2006 | Sullivan et al. | 600/529 |
| 7,011,092 B2 | 3/2006 | McCombs et al. | 128/205.12 |
| 7,032,589 B2 | 4/2006 | Kerechanin et al. | 128/200.24 |
| 7,063,084 B2 | 6/2006 | McDonald | 128/200.28 |
| 7,066,178 B2 | 6/2006 | Gunaratnam et al. | 128/206.21 |
| 7,066,985 B2 | 6/2006 | Deane et al. | 95/96 |
| 7,073,499 B1 | 7/2006 | Reinhold et al. | 128/200.18 |
| 7,086,366 B1 | 8/2006 | Killion | 123/192.2 |
| 7,118,536 B2 | 10/2006 | Haberland et al. | 600/538 |
| 7,121,276 B2 | 10/2006 | Jagger et al. | 128/201.21 |
| 7,168,429 B2 | 1/2007 | Matthews et al. | 128/204.21 |
| 7,171,963 B2 | 2/2007 | Jagger et al. | 128/201.21 |
| 7,183,681 B2 | 2/2007 | Segawa et al. | 310/68 B |
| 7,188,621 B2 | 3/2007 | DeVries et al. | 128/205.24 |
| 7,225,809 B1 | 6/2007 | Bowen et al. | 128/204.21 |
| 7,226,280 B1 | 6/2007 | Yokoi | 418/206.4 |
| 7,329,304 B2 | 2/2008 | Bliss et al. | 95/12 |
| 7,331,342 B2 | 2/2008 | Spearman et al. | 128/203.14 |
| 7,335,243 B2 | 2/2008 | Homan et al. | 55/385.2 |
| 7,351,034 B2 | 4/2008 | Cens et al. | 416/61 |
| 7,368,005 B2 | 5/2008 | Bliss et al. | 96/121 |

| | | | |
|---|---|---|---|
| 2001/0044588 A1 | 11/2001 | Mault | 600/549 |
| 2002/0134378 A1 | 9/2002 | Finnegan et al. | 128/200.24 |
| 2003/0057904 A1 | 3/2003 | Sacher | 318/268 |
| 2003/0208113 A1 | 11/2003 | Mault et al. | 600/316 |
| 2004/0074495 A1 | 4/2004 | Wickham et al. | 128/204.18 |
| 2004/0147818 A1 | 7/2004 | Levy et al. | 600/300 |
| 2004/0211422 A1 | 10/2004 | Arcilla et al. | 128/204.19 |
| 2004/0221854 A1 | 11/2004 | Hete et al. | 128/207.16 |
| 2004/0226562 A1 | 11/2004 | Bordewick | 128/204.23 |
| 2005/0112013 A1 | 5/2005 | DeVries et al. | 418/206.1 |
| 2005/0124866 A1 | 6/2005 | Elaz et al. | 600/301 |
| 2005/0166921 A1 | 8/2005 | DeVries et al. | 128/204.21 |
| 2005/0188991 A1 | 9/2005 | Sun et al. | 128/204.23 |
| 2005/0241642 A1 | 11/2005 | Krzysztofik | 128/206.15 |
| 2006/0065672 A1 | 3/2006 | LeCourt et al. | 222/3 |
| 2006/0069326 A1 | 3/2006 | Heath | 601/41 |
| 2006/0070624 A1 | 4/2006 | Kane et al. | 128/204.23 |
| 2006/0124128 A1 | 6/2006 | Deane et al. | 128/204.21 |
| 2006/0144396 A1 | 7/2006 | DeVries et al. | 128/204.21 |
| 2006/0144399 A1 | 7/2006 | Davidowski et al. | 128/205.21 |
| 2006/0144405 A1 | 7/2006 | Gunaratnam et al. | 128/206.21 |
| 2006/0150973 A1 | 7/2006 | Chalvignac | 128/214.21 |
| 2006/0174871 A1 | 8/2006 | Jagger et al. | 128/201.21 |
| 2006/0174872 A1 | 8/2006 | Jagger et al. | 128/201.21 |
| 2006/0174874 A1 | 8/2006 | Jagger et al. | 128/201.21 |
| 2006/0174875 A1 | 8/2006 | Jagger et al. | 128/201.21 |
| 2006/0174877 A1 | 8/2006 | Jagger et al. | 128/201.21 |
| 2006/0174878 A1 | 8/2006 | Jagger et al. | 128/201.21 |
| 2006/0174880 A1 | 8/2006 | Jagger et al. | 128/201.25 |
| 2006/0174881 A1 | 8/2006 | Jagger et al. | 128/201.25 |
| 2006/0174882 A1 | 8/2006 | Jagger et al. | 128/201.25 |
| 2006/0201503 A1 | 9/2006 | Breen | 128/204.18 |
| 2006/0213518 A1 | 9/2006 | DeVries et al. | 128/204.21 |
| 2006/0249149 A1 | 11/2006 | Meier et al. | 128/204.18 |
| 2006/0266355 A1 | 11/2006 | Misholi | 128/204.23 |
| 2006/0283450 A1 | 12/2006 | Shissler et al. | 128/204.21 |
| 2007/0044799 A1 | 3/2007 | Hete et al. | 128/205.11 |
| 2007/0062529 A1 | 3/2007 | Choncholas et al. | 128/204.22 |
| 2007/0062532 A1 | 3/2007 | Choncholas | 128/204.23 |
| 2007/0068526 A1 | 3/2007 | Lang et al. | 128/204.22 |
| 2007/0079826 A1 | 4/2007 | Kramer et al. | 128/200.14 |
| 2007/0113843 A1 | 5/2007 | Hughes | 128/200.24 |
| 2007/0113849 A1 | 5/2007 | Matthews et al. | 128/204.22 |
| 2007/0169776 A1 | 7/2007 | Kepler et al. | 128/200.23 |
| 2007/0181127 A1 | 8/2007 | Jin et al. | 128/204.21 |
| 2007/0193580 A1 | 8/2007 | Feldhahn et al. | 128/204.18 |
| 2007/0215146 A1 | 9/2007 | Douglas et al. | 128/200.24 |
| 2007/0221224 A1 | 9/2007 | Pittman et al. | 128/204.22 |
| 2007/0235030 A1 | 10/2007 | Teetzel et al. | 128/205.12 |
| 2007/0265877 A1 | 11/2007 | Rice et al. | 705/2 |
| 2007/0277825 A1 | 12/2007 | Bordewick et al. | 128/204.23 |
| 2008/0000474 A1 | 1/2008 | Jochle et al. | 128/204.18 |
| 2008/0029096 A1 | 2/2008 | Kollmeyer et al. | 128/204.21 |
| 2008/0035149 A1 | 2/2008 | Sutton | 128/205.24 |
| 2008/0039701 A1 | 2/2008 | Ali et al. | 600/301 |
| 2008/0066739 A1 | 3/2008 | LeMahieu et al. | 128/200.14 |
| 2008/0078395 A1 | 4/2008 | Ho et al. | 128/205.24 |
| 2008/0099017 A1 | 5/2008 | Bordewick et al. | 128/204.21 |
| 2008/0110455 A1 | 5/2008 | Dunsmore et al. | 128/200.24 |
| 2008/0110458 A1 | 5/2008 | Srinivasan et al. | 128/203.26 |
| 2008/0110462 A1 | 5/2008 | Chekal et al. | 128/204.26 |
| 2008/0127976 A1 | 6/2008 | Acker et al. | 128/204.18 |

FOREIGN PATENT DOCUMENTS

| | | |
|---|---|---|
| DE | 3414064 | 10/1985 |
| DE | 3620792 | 12/1987 |
| DE | 19817356 | 10/1999 |
| EP | 0239026 | 9/1987 |
| EP | 0521709 | 1/1993 |
| EP | 0938909 | 9/1999 |
| EP | 1130761 | 9/2001 |
| EP | 1243282 | 9/2002 |
| FR | 2875891 | 9/2004 |
| GB | 2157370 | 10/1985 |
| JP | 2001 050774 | 2/2001 |
| JP | 2003 124986 | 4/2003 |
| WO | WO 89/10768 | 11/1989 |
| WO | WO 92/11054 | 7/1992 |
| WO | WO 96/11717 | 4/1996 |
| WO | WO 97/11522 | 3/1997 |
| WO | WO 97/15343 | 5/1997 |
| WO | WO 99/64825 | 12/1999 |
| WO | WO 00/45883 | 8/2000 |
| WO | WO 02/11861 | 2/2002 |
| WO | WO 2004/040745 | 5/2004 |

OTHER PUBLICATIONS

Eaton—Supercharger Division, "Why An Eaton Supercharger?", www.eaton/comsuipercharger/whysuper.html.

* cited by examiner

METHOD AND APPARATUS FOR ATTENUATING COMPRESSOR NOISE

CROSS-REFERENCE TO RELATED APPLICATION

This patent application is a continuation-in-part of U.S. patent application Ser. No. 10/912,747, filed Aug. 4, 2004, now issued as U.S. Pat. No. 7,188,621, the specification and drawing figures of which are incorporated by reference herein, and which claims the benefit of U.S. Provisional Patent Application Ser. No. 60/492,421, filed Aug. 4, 2003.

FIELD OF THE INVENTION

The present invention relates to compressors, and more particularly to a method and apparatus for reducing the noise generated by compressors, including Roots-type blowers used in portable mechanical ventilators.

BACKGROUND OF THE INVENTION

Roots-type blowers have potential application in a wide variety of environments. They are relatively efficient, and can produce a wide range of delivery pressures and volumes. However, they produce a high level of noise. The high noise level produced by Roots blowers has limited their use in environments where such high noise levels are unacceptable. One such environment is providing breathing assistance to patients by means of a mechanical ventilator.

For a variety of reasons, there are instances when individuals (patients) with acute and chronic respiratory distress cannot ventilate themselves (i.e. breathe). In those circumstances, such patients require breathing assistance to stay alive. One solution is to provide those patients with a medical device called a mechanical ventilator, which assists with their breathing.

A purpose of a mechanical ventilator is to reproduce the body's normal breathing mechanism. Most mechanical ventilators create positive intrapulmonary pressure to assist breathing. Positive intrapulmonary pressure is created by delivering gas into the patient's lungs so that positive pressure is created within the alveoli (i.e. the final branches of the respiratory tree that act as the primary gas exchange units of the lung). Thus, a mechanical ventilator is essentially a device that generates a controlled flow of gas (e.g., air or oxygen) into a patient's airways during an inhalation phase, and allows gas to flow out of the lungs during an exhalation phase.

Mechanical ventilators use various methods to facilitate precise delivery of gas to the patient. Some ventilators use an external source of pressurized gas. Other ventilators use gas compressors to generate an internal source of pressurized gas.

Most ventilator systems that have an internal gas source use either constant speed or variable speed compressors. Constant speed compressors are usually continuously operating, rotary-based machines that generate a fairly constant rate of gas flow for ultimate delivery to the patient. These constant speed systems generally use a downstream flow valve to control flow of the gas to the patient, with a bypass or relief mechanism to divert excess flow that is at any time not needed by the patient (e.g. during exhalation).

Variable speed compressors operate by rapidly accelerating from a rest state to the rotational speed needed to produce the flow rate necessary during the beginning of the inhalation phase, and then decelerating to a rest or nearly rest state at the end of the inhalation phase to allow the patient to exhale.

Two types of variable speed compressor systems are typically employed in the mechanical ventilator art: piston-based systems and rotary-based systems. An example of a prior art variable speed compressor system for use in a mechanical ventilator is described in U.S. Pat. No. 5,868,133 to DeVries et al. This system uses drag compressors to provide the desired inspiratory gas flow to the patient.

Rotary compressor systems deliver the required gas flow during inhalation by accelerating the compressor rotor(s) to the desired speed at the beginning of each inspiratory phase and decelerating the compressor rotor(s) to a rest or nearly rest speed at the end of each inspiratory phase. Thus, the rotary compressor is stopped, or rotated at a nominal base rotational speed, prior to commencement of each inspiratory ventilation phase. Upon commencement of an inspiratory phase, the rotary compressor is accelerated to a greater rotational speed for delivering the desired inspiratory gas flow to the patient. At the end of the inspiratory phase, the rotational speed of the compressor is decelerated to the base speed, or is stopped, until commencement of the next inspiratory ventilation phase. Prior art systems typically use a programmable controller to control the timing and rotational speed of the compressor.

Great strides have been realized in reducing the size of mechanical ventilators. Ventilators are now available that are portable, and allow users a limited degree of autonomous mobility. Further reducing the size and power requirements of mechanical ventilators hold the potential of giving patients even greater freedom of movement, enhancing their quality of life.

Because of its relative efficiency, a Roots blower can potentially contribute to the reduction in size and power consumption of mechanical ventilators. However, heretofore it has not been possible to reduce the noise created by a Roots blower to the level that is acceptable for a mechanical ventilator.

Roots blowers use a pair of interacting rotors. Each rotor has two or more lobes. The rotors are rotated inside a housing having an inlet and an outlet. The rotors rotate with the lobes of one rotor moving into and out of the spaces between the lobes of the other. Gas is moved through the blower in chambers formed by adjacent lobes of a rotor and the adjacent rotor housing wall. These chambers will be referred to herein as "gas transport chambers."

Noise is generated by roots blowers in a number of ways. One type of noise is caused by pulsing flow. As the rotors rotate, the gas transport chambers between the lobes of each rotor are sequentially exposed to the outlet. As each chamber is exposed to the outlet, a lobe of the mating rotor rotates into the chamber, displacing the gas in chamber to the outlet, causing a flow/pressure pulse. In the case of a pair of rotors each having two lobes, during each cycle of the blower, there are four pulses generated by the displacement of gas by the gas transport chambers. These pulses generate a substantial amount of noise.

A second type of noise is generated by a phenomenon known as "flow back." As each rotor rotates, it inducts gas at low pressure at the inlet. This gas is generally trapped in the gas transport chambers as the rotor moves towards the outlet. When this pocket of gas initially reaches the outlet, it is exposed to higher pressure gas at the outlet. At that time, the higher pressure gas at the outlet rushes backwardly into the gas transport chamber that contains the lower pressure gas that is being delivered from the inlet.

Some attempts have been made to reduce the noise level of Roots blowers. To reduce the "pulsing" type of noise, the lobes of the rotors have been reconfigured so that they have a helical, rather than straight, shape. When the lobes of the rotors are straight, the gas flow into and out of the gas transport chamber is very abrupt. When the lobes are helical in shape, each lobe displaces gas over a larger angle of rotation. This spreads the displacement of gas over an angle of rotation, lessening the magnitude of the pressure pulse caused by the gas displacement, and reducing the noise created by the blower. However, this lobe design does not address the problem of flow back, since the relative pressure between the gas at the outlet and gas being delivered from the inlet is still the same.

Attempts have also been made to reduce flow back noise. Various kinds of channels or passages have been provided that allow some gas to flow from the outlet to the gas transport chamber prior to the time the chamber reaches the outlet, thereby increasing the gas pressure in the chamber and reducing the pressure spike that occurs when the gas in the chamber is exposed to the higher outlet pressure.

An example of a Roots blower configured with noise reducing flow-back channels is described in co-pending U.S. patent application Ser. No. 10/985,528. Although such flow-back channels are effective in reducing the level of noise, the resultant noise level may still not be sufficiently low for some mechanical ventilator applications. Accordingly, additional methods and apparatus for reducing Roots blower noise are desired.

SUMMARY OF THE INVENTION

The invention comprises a method and apparatus for reducing the noise generated by compressors, including Roots-type blowers. The invention has particular use for reducing noise generated by compressors used in mechanical ventilators, though the advantages thereof may be realized in many different applications, including in attenuating noise generated by devices other than compressors and Roots-type blowers and in other applications than mechanical ventilators in which noise attenuation is desired.

One embodiment of the invention comprises a noise-attenuating gas flow path for a compressor contained in a portable ventilator housing. In one embodiment, the gas flow path comprises an inlet flow path from an inlet of the ventilator housing to an inlet of the compressor, and/or an outlet gas flow path from an outlet of the compressor to an outlet of the ventilator housing. Each gas flow path includes a plurality of interconnected chambers. In one embodiment, the inlet flow path comprises at least two chambers interconnected by means of a flow tube. The dimensions of the chambers and the flow tubes are selected so that an impedance mismatch is created between the chambers and the flow tubes. In one embodiment, this impedance mismatch is created by sizing adjacent chambers so that they have a cross-sectional flow area substantially larger than the cross sectional area of the flow tube that interconnects the two chambers. This impedance mismatch reduces the amount of noise transmitted from one chamber to the next. The chambers and flow-tubes may be configured in a folded flow-path that allows the flow path to fit into a housing of limited space, such as a portable ventilator housing.

In one embodiment of the invention, the flow path comprises one or more perforated tubes. In one embodiment, one or more perforated tubes are located in one or more of the chambers comprising the gas inlet and/or outlet flow paths.

In one embodiment, the perforated tube is configured to provide a large impedance mismatch without excessively impeding gas flow.

In one embodiment, the perforated tube has at least one exterior tube extending from the tube wall through which gas exits. The cross-sectional area of the at least one exterior tube is substantially reduced compared to the effective flow area of both the inlet chamber of the perforated tube and chamber in which the perforated tube is located. In this manner, impedance mismatches are created between the inlet chamber and the exterior tubes and between the exterior tubes and the chamber in which the perforated tube is located, which are useful in attenuating noise. In addition, to prevent flow of gas along the flow path that includes the perforated tube from being substantially impeded by the small cross-sectional area of the exterior tube, in one embodiment, the perforated tube includes a plurality of exterior tubes. In this configuration, an impedance mismatch is created relative to each exterior tube, but the total cross-sectional flow area through the perforated tube via the multiple exterior tubes remains relatively large.

One embodiment of the invention comprises a noise attenuating mounting system for a compressor. The mounting system comprises flexible mounts that cooperate to dampen vibrations generated by the compressor. In one embodiment, a plurality of mounts are positioned between a housing of the compressor and a supporting structure, such as the walls of a compartment of a mechanical ventilator in which the compressor is disposed.

In one embodiment, the mounts comprise a connecting member that is connected to the compressor housing and a damping member that is positioned between the connecting member and the supporting structure.

Each mount is configured so that the natural frequency of the blower and its associated mounts, when assembled, is below the frequency of the forces that are to be damped. In one mechanical ventilator environment, the blower is generally configured to operate at relatively high speeds, from about 6000 rpm to about 20,000 rpm, and the mounts are configured such that the compressor/mount assembly has a natural frequency below the range of about 10 Hz. In one embodiment, the mounts are constructed of silicon rubber having a hardness of about 70 shore.

Further objects, features, and advantages of the present invention over the prior art will become apparent from the detailed description that follows, when considered with the attached figures.

DETAILED DESCRIPTION OF THE INVENTION

The invention comprises a method and apparatus for attenuating or reducing noise generated by compressors, including Roots-type blowers. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

In general, the invention comprises a method and apparatus for reducing or attenuating generated noise. The invention has particular application to reducing or attenuating noise generated by compressors used in noise-sensitive environments, such as, for example, a Roots-type blower used in a portable mechanical ventilator. One embodiment of the invention comprises a specially configured gas inlet path from an inlet of a housing in which the compressor is disposed to an inlet of the compressor, and/or a specially configured gas outlet path from an outlet of the compressor to an outlet of the housing in which the compressor is disposed. In one embodiment, the path(s) include one or more chambers and connecting tubes configured to reduce the noise generated by the compressor. In one or more embodiments, the invention comprises one or more noise attenuating perforated tubes. The perforated tubes may be disposed along the inlet and/or outlet paths to reduce the noise generated by the compressor. In one or more embodiments, the invention comprises a compressor mounting system comprising one or more shock absorbing or damping elements.

As described below, the various embodiments of the noise-reducing method and apparatus of the invention may be used together or apart from one another to reduce the noise generated by a compressor. It will also be appreciated that the invention may have application in other environments, including compressors used in noise sensitive environments other than in mechanical ventilators.

The method and apparatus of the invention are "external" in the sense that they are located outside of the compressor or other device that is the source of the noise to be attenuated. This contrasts to "internal" noise attenuating techniques, such as the Roots-type blower configuration described in co-pending U.S. patent application Ser. No. 10/985,528 filed Nov. 10, 2004, incorporated by reference herein.

Figure 1:
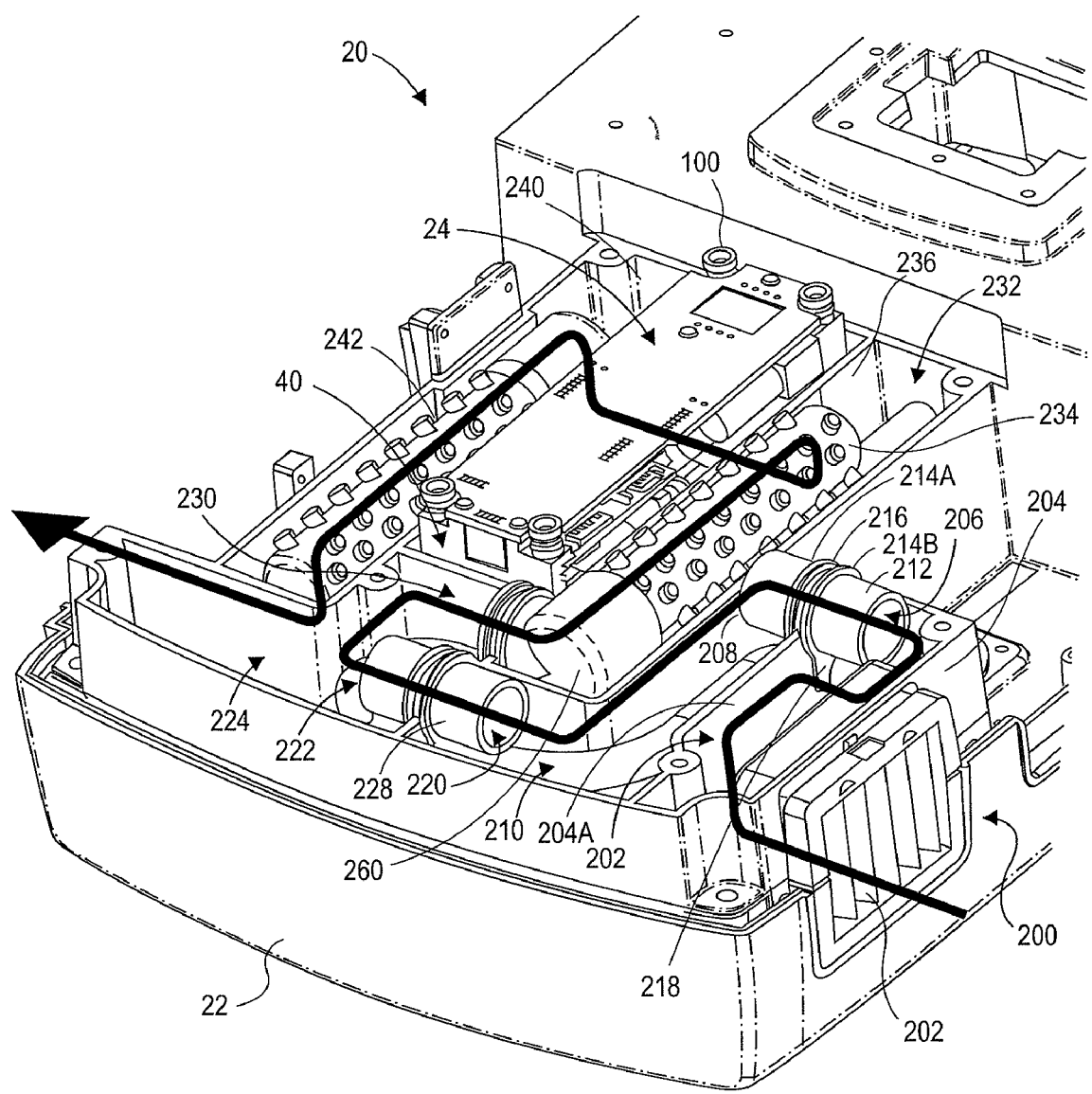
FIG. 1 is a perspective view of a mechanical ventilator comprising one embodiment of the invention.

FIG. 1 illustrates the portion of a portable mechanical ventilator 20 containing a compressor 24 and inlet and outlet flow paths of an embodiment of the invention. Ventilator 20 comprises one environment in which the noise reducing method and apparatus of the invention may be used.

The mechanical ventilator 20 illustrated in FIG. 1 comprises a housing 22 containing or supporting a plurality of components. FIG. 1 is a rear view of the housing illustrating the ventilator 20 with a rear cover portion of the housing 22 removed to expose various components located within the housing 22.

It will be appreciated that mechanical ventilators 20 generally include a great number of components. Various of those components do not comprise portions of the present invention, and as such are not described in detail herein. For example, the ventilator 20 includes a plurality of gas flow control equipment, including circuitry, input buttons and the like.

As illustrated in FIG. 1, a particular example of the compressor 24 suitable for use with the ventilator 20 includes a Roots-type blower. In one embodiment, the compressor 24 is of the type described and illustrated in co-pending U.S. application Ser. No. 10/985,528 filed Nov. 10, 2004, which is incorporated in its entirety herein.

Figure 2:
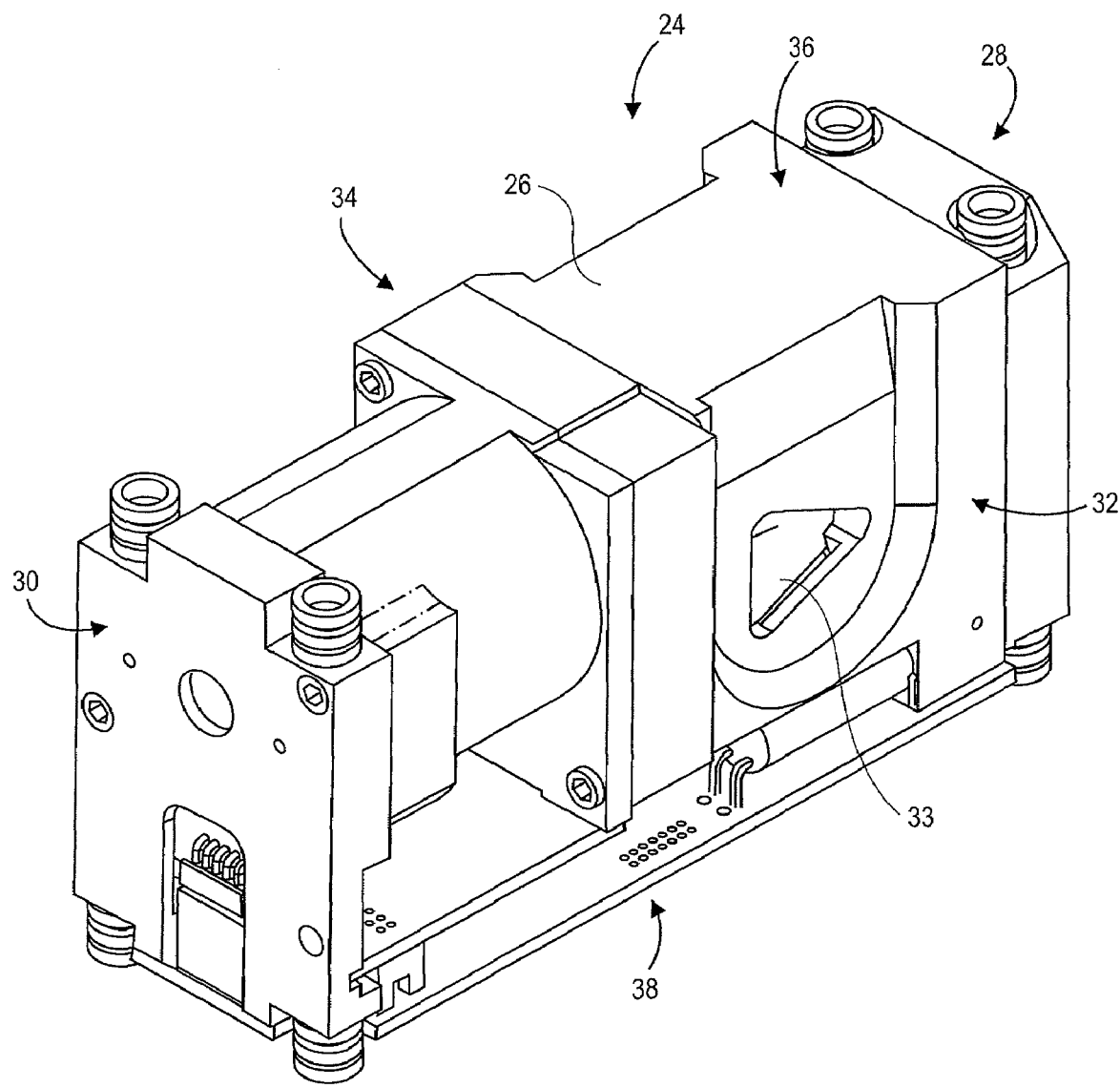
FIG. 2 is a perspective view of a housing for a Roots-type blower comprising a plurality of flexible mount of an embodiment of the invention.

In the embodiment of FIG. 1, the compressor 24, including its associated drive motor, is mounted within a housing 26 (shown in FIG. 2). The housing 26 may have a wide variety of configurations. Referring to FIG. 2, in one embodiment, the housing 26 is generally rectangular in shape, having first and second opposing ends 28,30, a first and a second opposing side 32,34, and a top 36 and a bottom 38. The housing 26 may have a great number of other shapes and configurations.

As is known in the art, the compressor 24 has an outlet 33 and an inlet (not visible in FIG. 2). In the embodiment illustrated in FIG. 2, the outlet 33 is located at the first side 32 and the outlet is located at the second side 34 of the housing 26 of the compressor 24.

As illustrated in FIG. 1, the compressor 24 is mounted in the ventilator housing 22. In one embodiment, the compressor 24 is mounted in a blower chamber or compartment 40. Details of the compartment 40 are provided below.

Gas Flow Paths

One or more embodiments of the invention comprise one or more noise-attenuating gas flow paths. In one embodiment, the gas flow path comprises an inlet gas flow path from an inlet of a housing in which a compressor is disposed to an inlet of the compressor, and/or an outlet gas flow path from the outlet of the compressor to an outlet of the housing. In one embodiment of the invention, the compressor is part of a mechanical ventilator, and the housing is the mechanical ventilator housing. In one embodiment, the compressor is a Roots-type blower.

Referring to FIG. 1, in one embodiment, a gas flow path is provided from an inlet port 200 of the ventilator housing 22 to an inlet of the compressor 24. A second gas flow path is provided from an outlet of the blower to an outlet of the ventilator housing.

In one embodiment, an inlet and/or outlet gas flow path includes one or more chambers interconnected by one or more flow tubes configured to create impedance mismatches at each tube/chamber interface that reduce the noise generated by the blower. As used herein, the terms "chamber" and "flow tube" refer to any passage configured so as to allow the flow of gas there through. FIG. 1 illustrates one embodiment of such a flow path. As illustrated, a first point of the flow path comprises an inlet port 200 in a ventilator housing 22. In one embodiment, the port 200 may include a filtration element 202, as is known to those of ordinary skill in the art.

Inlet port 200 provides a flow path to a first chamber 202. The first chamber 202 is defined by one or more walls 204. The walls 204 may comprise a portion of the ventilator housing 22, such as by being integrally molded. In one embodiment, the first chamber 202 is generally enclosed when the compressor 24 is in use. Thus, in the embodiment illustrated, a cover (not shown) in one embodiment forms a portion of the housing 22 and forms a top portion of the chamber 202 during use. In operation, gas enters first chamber 202 through port 200 and exits through an outlet port 206 leading from the chamber.

The configuration of the first chamber 202, including its shape and size, may vary. As described in more detail below, the configuration of the first chamber 202 may in one embodiment be determined so that the first chamber 202 is effective in attenuating noise at one or more frequencies.

In the embodiment illustrated, the outlet port 206 from the first chamber 202 comprises an inlet to a flow tube 212. An outlet port 208 of flow tube 212 forms an inlet to a second chamber 210. In one embodiment, the gas flow area of the passage defined by the flow tube 212, or at least of outlet port 206 and/or inlet port 208 thereof, is substantially smaller than the respective gas flow areas of first and second chambers 202,210. In this manner, an impedance mismatch is created. This impendence mismatch attenuates the sound generated by the compressor 24 that is transmitted along the inlet gas flow path to the compressor 24.

In one embodiment, flow tube 212 comprises a generally circular wall defining a central passage. The passage has a first end corresponding to the outlet port 206 and a second end corresponding to the inlet port 208.

In one embodiment, the flow tube 212 is mounted to the ventilator housing 22 and, more particularly, in or to a dividing wall 204a dividing the first chamber 202 and second chamber 210. As illustrated, the tube 212 has a pair of flanges 214a,b. In one embodiment, the flanges 214a,b are annular and spaced from one another to define a slot 216 there between. The slot 216 is of sufficient width to fit into a semi-circular opening formed in the dividing wall 204a that divides the first and second chambers 202,210.

As illustrated, in an embodiment in which the ventilator housing 22 includes a removable cover, a portion of the dividing wall 204a is connected to or formed as part of the cover, and part is connected to or formed as part of the housing 22. The flow tube 212 extends through a semi-circular opening in the dividing wall 204a. In the embodiment illustrated, a portion of an opening through which the flow tube 212 extends is formed in the portion of the dividing wall associated with the cover, and the remaining portion of the opening is defined by the portion of the dividing wall associated with the main portion of the housing 22. In this manner, as illustrated, when the cover is removed, the flow tube 212 is accessible and may be removed from the housing 22, such as by lifting it out of engagement with the portion of the dividing wall 204a associated with the housing 22.

As illustrated in FIG. 1, one or more tabs 218 may extend from the flow tube 212. The tabs 218 in one embodiment help ensure correct placement of flow tube 212 during assembly. In one embodiment, the tabs 218 comprise generally planar elements that are integrally formed with the flow tube 212, and more particularly, are formed as extensions of flanges 214a,b.

The flow tube 212 may be constructed from a variety of materials and in a variety of ways. In one embodiment, the flow tube 212 is constructed of flexible urethane material.

In the embodiment of FIG. 1, gas flows to the second chamber 210 from the first chamber 202 via the flow tube 212. In one embodiment, the second chamber 210 has an outlet port 220 which leads to an inlet port 222 of a third chamber 224. Like the first and second chambers 202,210, the second and third chambers 210,224 are in one embodiment linked by a connecting flow tube 228, similar in form to flow tube 212 described above. The flow tube 228 spans a dividing wall 229 between the second and third chambers 210,224. The cross sectional flow area of flow tube 228, like that of flow tube 212, is chosen such that an impedance mismatch is created between chamber 210 and flow tube 228 and between flow tube 228 and chamber 224. These impedance mismatches further reduce the noise generated by compressor 24.

In one embodiment, the third chamber 224 has an outlet port 230 that leads to a fourth chamber 232. In the embodiment illustrated in FIG. 1, the outlet port 230 of the third chamber 224 leads to a perforated tube 234 disposed within a fourth chamber 232. Details of the perforated tube 234 are described in more detail below. Gas flows from the third chamber 224 through the perforated tube 234 into the fourth chamber 232.

In the embodiment of FIG. 1, a second perforated tube (not visible in FIG. 1) is disposed in the fourth chamber 232 underneath perforated tube 234. This second perforated tube is in communication with the fourth chamber 232 and the inlet to the compressor 24. As described above, the compressor 24 is located in a compartment 40 defined by one or more walls. In one embodiment, the fourth chamber 232 and the compartment 40 are separated at least in part by a dividing wall 236. An opening (not shown) is provided in the dividing wall 236, allowing the second perforated tube to mate with the inlet to the compressor 24 such that gas may flow from the fourth chamber 232 through the second perforated tube to the inlet of the compressor 24.

In the embodiment of FIG. 1, an inlet flow path is defined from a point outside of the ventilator housing 22 through the first, second, third and fourth chambers 202,210,224,232, flow tubes 212 and 228, perforated tube 234 and the second perforated tube to the inlet of the compressor 24. Gas flows through this path from outside ventilator housing 22 to the compressor 24.

As detailed above, the size of one or more of the chambers 202,210,224,232 and flow tubes 212 and 228 are in one embodiment selected so that multiple impedance mismatches are created along the inlet flow path to the compressor 24. In one embodiment, these impedance mismatches are created by sizing the chambers so that their respective cross-sectional gas flow areas are substantially larger than the corresponding cross-sectional flow areas of the flow tubes interconnecting the chambers.

In one or more embodiments, it is desirable to make the ventilator housing 22 generally as small as possible so as to reduce the total size or dimensions of the ventilator 20. Of course, various of the components of the ventilator occupy space in the housing 22, such as the control circuitry, the Roots-type blower and the like. This leaves only a finite mount of space within the housing 22 for the noise attenuating flow path of the invention.

In one embodiment, the size and shape of the chambers, and their configuration, is to some extent limited by the size and shape of the ventilator housing 22 and the location of the other components. In one embodiment, the size of the chambers, including their location, is selected to attenuate noise of specific frequencies. For example, the size and shape of the second chamber 210 may be selected so that the impedance mismatch between chamber 210 and flow tube 228 substantially eliminates noise generated by the Roots-type blower at one or more first frequencies. The size and shape of the third chamber 224 may be selected so that the impedance mismatch between chamber 224 and perforated tube 234 substantially eliminates noise generated by the Roots-type blower at one or more second frequencies different from the first frequency(ies).

In the configuration just described, a plurality of chambers and connecting flow tubes are selected to reduce the noise generated by a Roots-type blower at a plurality of frequencies. It will be appreciated that there may be a greater or lesser number of chambers and connecting flow tubes. Of course, the number, size, shape of chambers and flow tubes and the configuration of the resulting flow path may depend upon the available space for the chambers within the ventilator housing 22. For example, a finite space may remain to define the inlet flow path once the housing size is fixed and the other components are associated with the housing. It may be found that as few as one or as many as four or more chambers may be arranged in this space to meet the desired goals. The use of multiple chambers and flow tubes allows the creation of a flow path that does not have to be linear, but that can be "folded," as in the embodiment of FIG. 1, to fit within the limited size and shape of space available in a housing or other enclosure, such as the portable ventilator housing of FIG. 1. The flow path is "folded" in the sense that it is configured to provide at least one change in direction of the gas flow along the flow path. For example, in the embodiment of FIG. 1, the gas flow path is configured to provide a plurality of changes in direction of approximately 90 degrees. Certain portions of the flow path of FIG. 1 provide a change in direction of greater than 90 degrees, including portions that provide a change in direction of approximately 180 degrees (for example the portion of the flow path that comprises flow tube 228 and chamber 224) and approximately 270 degrees (for example the portion of the flow path that comprises chamber 210, flow path 228, and chamber 222). The shape of the chambers may be generally rectangular, or may have irregular shapes, such as, for example, the "dogleg" shape of chambers 210 and 224 in the embodiment of FIG. 1.

In one embodiment, a flow path is defined from an outlet of the compressor 24 to a second point. In the embodiment of FIG. 1, this second point comprises an outlet of the ventilator housing 22.

In one embodiment, an outlet of the compressor 24 leads to a fifth chamber 240. In one embodiment, an opening is provided in a wall forming the compartment 40 in which the compressor 24 is located. The opening is in one embodiment aligned with the outlet of the compressor 24.

In one embodiment, expelled gas is directed from the outlet of compressor 24 through a pair of perforated tubes (perforated tube 242 and a fourth perforated tube, not visible in FIG. 1, that is disposed in fifth chamber 240 underneath perforated tube 242) arranged in a similar manner to the two perforated tubes disposed inside fourth chamber 232. The expelled gas flows from the outlet of the blower through the fourth peforated tube (not shown) into the fifth chamber 240. From the fifth chamber 240, it is routed through perforated tube 242 to a ventilator outlet. In one embodiment, the ventilator outlet includes a nipple or connector to which a delivery tube (not shown) may be connected. The delivery tube is in one embodiment used to deliver gas to a user of the ventilator 20.

In the embodiment of FIG. 1, the outlet flow path leads from the compressor 24 via the fourth perforated tube (not visible) to the fifth chamber 240, and from there via perforated tube 242 to the ventilator outlet. In other embodiments, the outlet flow path may not include a chamber at all, but simply a passage to the outlet. In addition, the outlet flow path might include a plurality of noise attenuating chambers and flow tubes, in a fashion similar to the inlet path described above.

In one embodiment it has been found that substantial noise attenuation is provided by an elongate delivery tube that is connected to the outlet of the ventilator 20 to deliver gas to the patient. In embodiments in which such an externally connected tube is used, less noise attenuation need be created along the outlet flow path from the outlet of the compressor 24 to the outlet of the housing 22 than along the inlet flow path from the inlet port 200 of housing 22 to the inlet of the compressor 24, because additional noise attenuation is provided externally by the delivery tube.

The configuration of the outlet flow path is in one embodiment is particularly configured to stay within the space which is available for the housing 22, while attenuating the particular frequency(ies) of noise desired to be attenuated. The outlet flow path may be linear, or may be "folded" in the same manner as the inlet flow path.

Various techniques may be utilized to determine the optimum configuration for the inlet and outlet paths in relation to noise attenuation. As described, in one embodiment, the size and shape of the ventilator housing overall may be dictated by a number of factors. The configuration of the inlet and outlet flow paths may then be determined, given the set amount of space that remains.

In one embodiment, iterations of flow path configurations may be performed to determine the best noise-attenuating configuration overall for the particular operational parameters of the blower or compressor. In one embodiment, life-size models of each chamber and flow tube are connected in a linear fashion to construct a flow path prototype. The prototype flow path is connected to the Roots-type blower or other compressor and tested at the desired operating ranges of the compressor. Changes in number, sizes, and configurations of the chambers and flow tubes may be iteratively made to determine the combination that produces the most satisfactory noise attenuation.

While the ventilator 20 illustrated in FIG. 1 has both a particularly configured noise-attenuating inlet flow path and outlet flow path, the ventilator 20 may be provided with only one or the other flow paths. It will also be appreciated that gas flow paths having the characteristics described above may be used in other environments, including with other types of blowers or compressors and in environments other than mechanical ventilators.

Perforated Tube

One or more embodiments of the invention comprise a noise-attenuating perforated tube. The perforated tube provides a gas flow path, while at the same time attenuating noise that is transmitted through the flowing gas. As described above, the perforated tube may be utilized in conjunction with a gas flow path to or from a Roots-type or other blower or compressor, for attenuating the noise generated thereby.

Figure 7:
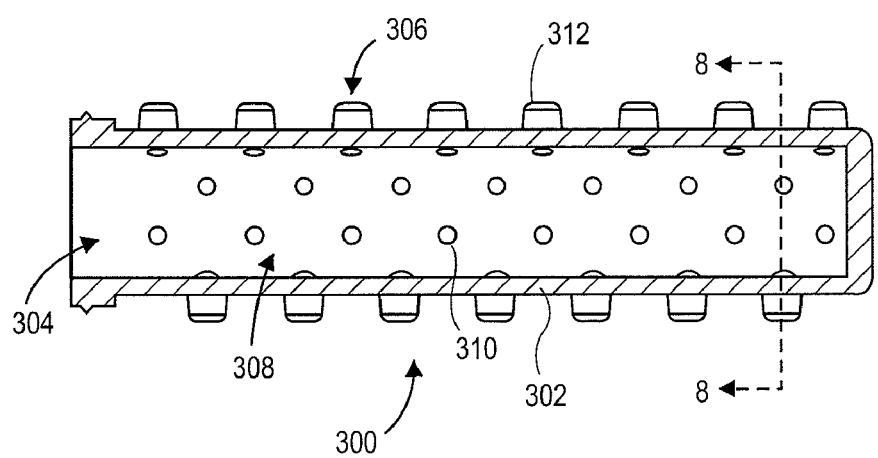
FIG. 7 is a cross-sectional view of the perforated tube illustrated in FIG. 6 taken along line 7-7 therein.
Figure 8:
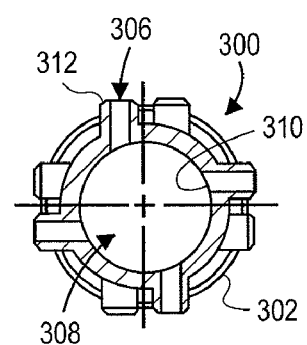
FIG. 8 is a cross-sectional view of the perforated tube illustrated in FIG. 7 taken along line 8-8 therein.
Figure 6:
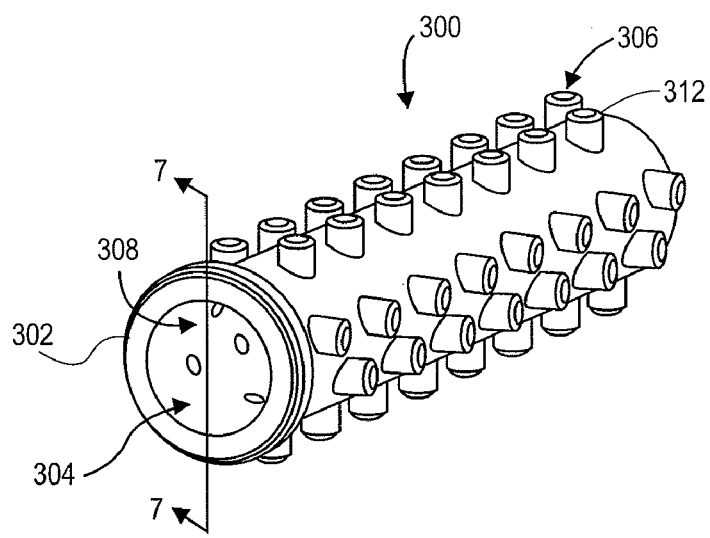
FIG. 6 is a perspective view of a perforated tube in accordance with one embodiment of the invention.

One example of a perforated tube according to an embodiment of the invention is illustrated in FIGS. 6-8. In one embodiment, the perforated tube 300 comprises a body 302 defining at least one port 304 and a plurality of exterior tubes 306 that form passages from an interior of body 302 to an exterior of body 302. Depending on the direction of gas flow through perforated tube 300, port 304 may act as either an inlet or an outlet port, and exterior tubes 306 may form flow passages out of or into perforated tube 300.

As illustrated in FIG. 6, the port 304 in one embodiment comprises a circular port defined by a generally circular wall portion of the body 302.

The port 304 leads to an interior chamber 308 defined by the body 302. The plurality of exterior tubes 306 are also in communication with the interior chamber 308, whereby a flow path is defined from the port 304 via the interior chamber 308 to and through the plurality of exterior tubes 306 or from the exterior tubes 306 via the interior chamber 308 through port 304, depending on the direction of gas flow.

In one embodiment, as illustrated in FIG. 1, the port 304 is connected to a right-angle tube 260 that defines a pathway from a first chamber through a dividing wall, in similar fashion to the tubes 212 and 228 described above. As illustrated in FIG. 1, this allows the port 304 to be in communication with one chamber, while the main portion of the body of the perforated tube, including the at least one exterior tube, is positioned inside another chamber.

In one or more embodiments, the body 302 includes a plurality of exterior tubes 306 each of which has a cross-sectional flow area that is substantially smaller than the diameter of body 302. In this manner, an impedance mismatch is created between the cross-sectional flow area of internal chamber 308 and each exterior tube 306 that is useful in attenuating noise.

To prevent the flow of gas along the flow path that comprises the perforated tube 300 from being substantially impeded by the small size of each exterior tube 306, in one embodiment, the perforated tube 300 includes a plurality of exterior tubes 306 that collectively provide a sufficient total flow area so that any impediment to gas flow is reduced. In this configuration, an impedance mismatch is created relative to each exterior tube 306, but the total flow rate of gas through the perforated tube 300 via the multiple exterior tubes 306 remains substantially unimpeded.

In one embodiment, each exterior tube 306 comprises a flow path of reduced diameter (compared to the diameter of internal chamber 308) having a length. In one embodiment, each exterior tube flow path has a first end 310 at the interior chamber 308, and a second end 312 that extends beyond the external dimension of body 302. This length provides additional noise attenuation benefits.

In one embodiment, each exterior tube 306 is defined by a cylindrical projection that extends outwardly from the body 302. In this manner, as illustrated in FIG. 1, the amount of space within the chamber in which the perforated tube 300 is located that is not occupied by the perforated tube is greater than if the length of the exterior tube flow path were provided solely by a wall thickness of body 302 (which would require a wall thickness equal to the exterior tube length). As will be appreciated, the exterior tube flow path could have a length defined by a passage through a thick wall comprising the body of the perforated tube. Compared to the embodiment illustrated in FIG. 1, this would result in the body occupying a substantially greater amount of space. In a case such as that illustrated where the size of the chamber in which the perforated tube is located is limited, such a configuration would substantially reduce the unoccupied volume of the chamber in which the perforated tube is located. If the size of the chamber were so reduced, the noise-attenuating impedance mismatch that results from the difference in flow area between the chamber and a connecting flow tube (such as flow tubes 306 of perforated tube 300) would be reduced.

One embodiment of the invention comprises a method of fabricating the perforated tube 300. In one embodiment, the perforated tube is molded from a two-piece mold. When the perforated tube leaves the mold, the body is generally cylindrical in exterior shape with a wall thickness equal to the length of the flow paths of exterior tubes 306. Thereafter, material comprising the body is removed except in the areas of the exterior tubes 306, thus forming the cylindrical projections shown in FIGS. 6-8.

The perforated tube 300 of the invention may be constructed in a variety of other manners and may be constructed from a variety of other materials. For example, the perforated tube could be constructed using a multi-piece mold that directly forms the perforated tube into the shape and configuration illustrated in FIGS. 6-8. The perforated tube could have a rectangular cross-section instead of the circular cross section shown in FIGS. 6-8. In one embodiment, the perforated tube 300 is constructed from a durable and resilient material, such as an ABS thermoplastic.

In one or more embodiments, the perforated tube 300 is configured to be located in a chamber or compartment. In one embodiment, as illustrated in FIG. 1, the perforated tube is located in a chamber along a flow path to or from a Roots-type blower or other compressor. In such a configuration, the size of the chamber may be selected so that the chamber housing the perforated tube creates an impedance mismatch with the exterior tubes of the perforated tube and with the next and/or preceding element in the gas flow path. In one or more embodiments, a multiple perforated tubes may be disposed in the same chamber, forming a gas flow path through the first perforated tube into the chamber, and then through the second perforated tube out of the chamber.

The configuration of the perforated tube and/or the chamber in which it is disposed may be selected so that the impedance mismatch results in an attenuation of noise at one or more frequencies or frequency ranges. For example, referring again to FIGS. 6-8, the size and number of the exterior tubes 306, including their location, may be selected relative to the desired gas flow rate, chamber size and the amount of noise attenuation desired and the frequencies of noise that are to be attenuated. For example, changing the cross-sectional area and/or length of the exterior tubes 306 will typically result changes in noise attenuation characteristics of the perforated tube.

The aggregation of flow path components of the invention (chambers, flow tubes, perforated tubes, gas delivery hose) allows noise to be attenuated at a variety of frequencies or frequency ranges. For example, in the embodiment illustrated in FIG. 1, each of the various noise attenuating components along the flow paths to and from the compressor 24 may be selected so that the components (in cooperation with adjacent components) attenuate noise at one or more frequencies or frequency ranges, and collectively the noise is attenuated over a variety of frequencies or frequency ranges.

In one embodiment of the invention, the configuration of the noise attenuating components illustrated in FIG. 1 are as shown in Table 1:

TABLE 1

| Component | Configuration | Dimensions (inches, approx.) |
|---|---|---|
| Chamber 202 | Rectangular | 3.0 long × 0.4 wide × 2.0 deep |
| Flow Tube 212 | Cylindrical | 0.4 diameter × 0.9 long |
| Chamber 210 | Dogleg | 2.0 deep × 0.9 wide × 3.1 leg, 1.9 leg |
| Flow Tube 228 | Cylindrical | 0.4 diameter × 0.9 long |
| Chamber 224 | Dogleg | 2.0 deep × (3.4 leg × 0.9 wide, 1.8 leg × 1.4 wide) |
| Perforated tubes (all) | Cylindrical body with external tubes | Body: 0.5 in diameter × 2.7 long Tubes: 0.14 diameter × 0.14 long, 0.6 dia. bore |
| Chamber 232 | Rectangular | 4.7 long × 0.9 wide × 2.0 deep |
| Chamber 240 | Rectangular | 4.7 long × 0.9 wide × 2.0 deep |

Noise Attenuating Mounting

One or more embodiments of the invention comprise a noise reducing component mounting system. One embodiment comprises a method and apparatus for mounting a compressor such as compressor 24 so as to isolate the compressor assembly (including its housing and electric motor), from the housing or frame to which the compressor assembly is mounted. In one embodiment, as illustrated in FIGS. 1 and 2, one or more damping elements are located between the housing 26 of the compressor 24 and the ventilator housing 22 or other support structure in which the blower is located.

Figure 3:
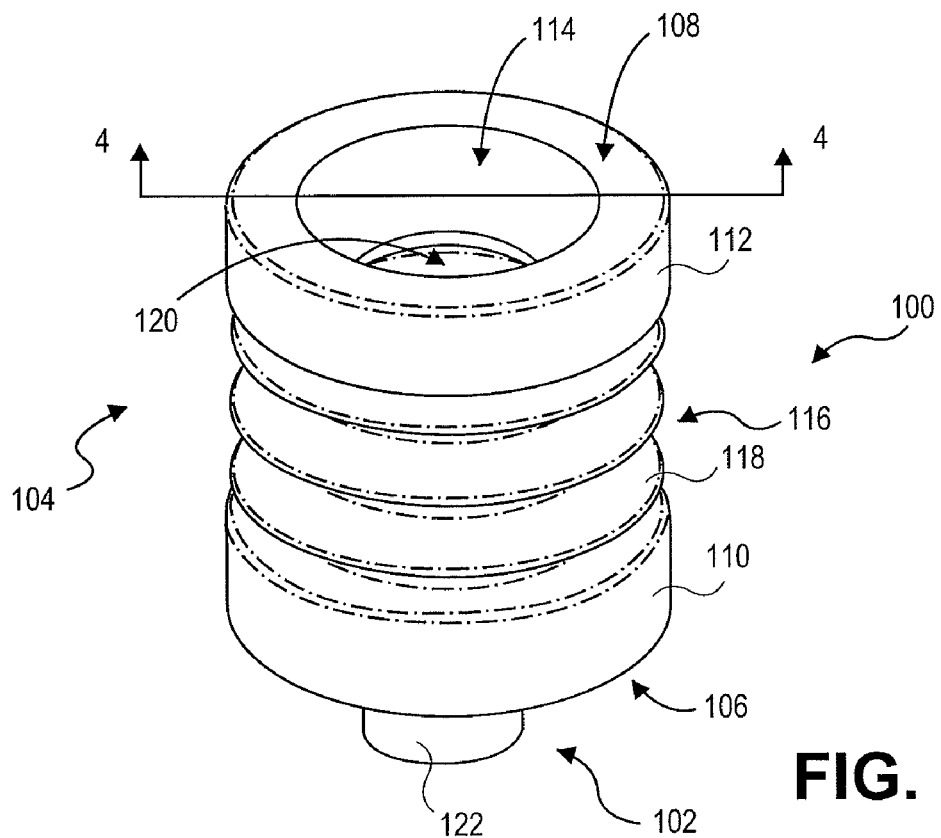
FIG. 3 is a perspective view of one of the flexible mounts illustrated in FIG. 2.
Figure 4:
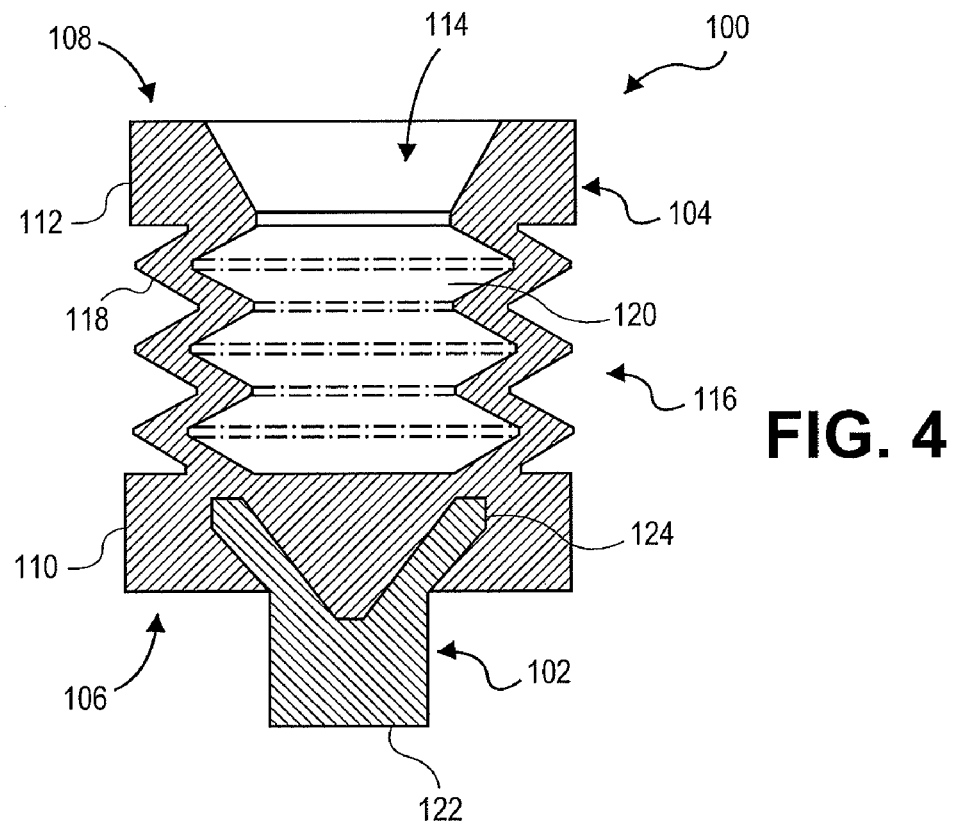
FIG. 4 is a cross-sectional view of the flexible mount illustrated in FIG. 3 taken along line 4-4 therein.

As illustrated in FIGS. 3 and 4, in one embodiment, the damping elements comprise resilient mounts 100. In one embodiment, each resilient mount 100 comprises a supporting member and a damping member. Each resilient mount 100 is configured so that the natural frequency of the blower assembly, when mounted to the ventilator housing 22 by means of resilient mounts 100, is below the frequency of the forces which are intended to be damped. In one embodiment, the resilient mounts 100 are configured to damp forces generated by compressor 24 during its operation.

In one embodiment in which the compressor 24 is used in a mechanical ventilator, the compressor 24 is generally configured to operate at speeds from about 6000 rpm to about 20,000 rpm. The frequency range of the forces generated by operation of the blower may be calculated or measured. In one embodiment, the resilient mounts 100 are configured to provide the blower/blower housing assembly with a natural frequency below 10 Hz.

Still referring to FIGS. 3 and 4, in one embodiment, each resilient mount 100 comprises a support member 102 and a damping member 104. In one embodiment, the damping member 104 comprises a resilient, bellows-shaped element. The damping member 104 has a first end 106 and an opposing second end 108. In one embodiment, the first end 106 comprises a first support portion 110 of the damping member 104, and the second end 108 comprises a second support portion 112 of the damping member 104.

As illustrated, the first support portion 110 comprises a generally solid, cylindrical portion of damping member 104. The first support portion 110 is configured to engage the support member 102, described in more detail below.

The second support portion 112 comprises an annular member defining a central opening 114. In one embodiment, as illustrated in FIGS. 3 and 4, central opening 114 is tapered such that the diameter of the opening increases moving in the direction of second end 108 of the damping member 104.

A flexible or resilient bellows-shaped portion 116 is located between the first and second support portions 110,112 of the damping member 104. As illustrated, this portion 116 comprises a generally annular member defined by a foldable wall 118. The foldable wall 118 extends between first support portion 110 and second support portion 112 of the damping member 104.

As illustrated, the foldable wall 118 defines a plurality of bellows or accordion-shaped elements that allow the foldable wall 118 to expand and contract in the axial direction between the first and second support portions 110,112.

The foldable wall 118 defines an internal space 120 that is in communication with the opening 114 of the damping member 104.

In one embodiment, the support member 102 is configured to attach the damping member 104 to the blower housing 26. In the embodiment of FIG. 4, the support member 102 is a Phillips head, flathead screw.

In one embodiment damping member 104 is constructed of silicon rubber having a hardness of about 70 shore. In one or more embodiments, the support member 102 and damping member 104 may each be molded as separate elements, and then assembled together to form the resilient mount 100. The resilient mount 100 may have a plurality of sizes/configurations and damping characteristics. In one embodiment, the size/configuration of the resilient mount 100 is selected to provide a particular degree of damping, when considering the mass of the compressor assembly and the forces generated by the compressor, and the total number of resilient mounts 100 which are to be used. In one embodiment, each resilient mount 100 is about 0.3 in. tall and has a diameter of about 0.25 in. As indicated above, the size, shape and materials of the resilient mounts 100 are selected so that the compressor assembly when mounted on resilient mounts 100 has a natural frequency less than the frequency of the forces generated by the compressor that are to be damped.

Referring to FIGS. 1 and 2, in one embodiment, a plurality of resilient mounts 100 are positioned between the top 36 of the blower housing 26 and the ventilator housing 22, and between the bottom 38 of the blower housing 26 and the ventilator housing 22. In the embodiment illustrated in FIG. 1, in which compressor 24 is located in a compartment 40, resilient mounts 100 are position between the blower housing 26 and the bottom of the compartment 40, as defined by the ventilator housing 22, and a top of the compartment 40 as defined by a cover portion (not shown) of the housing 22.

Figure 5:
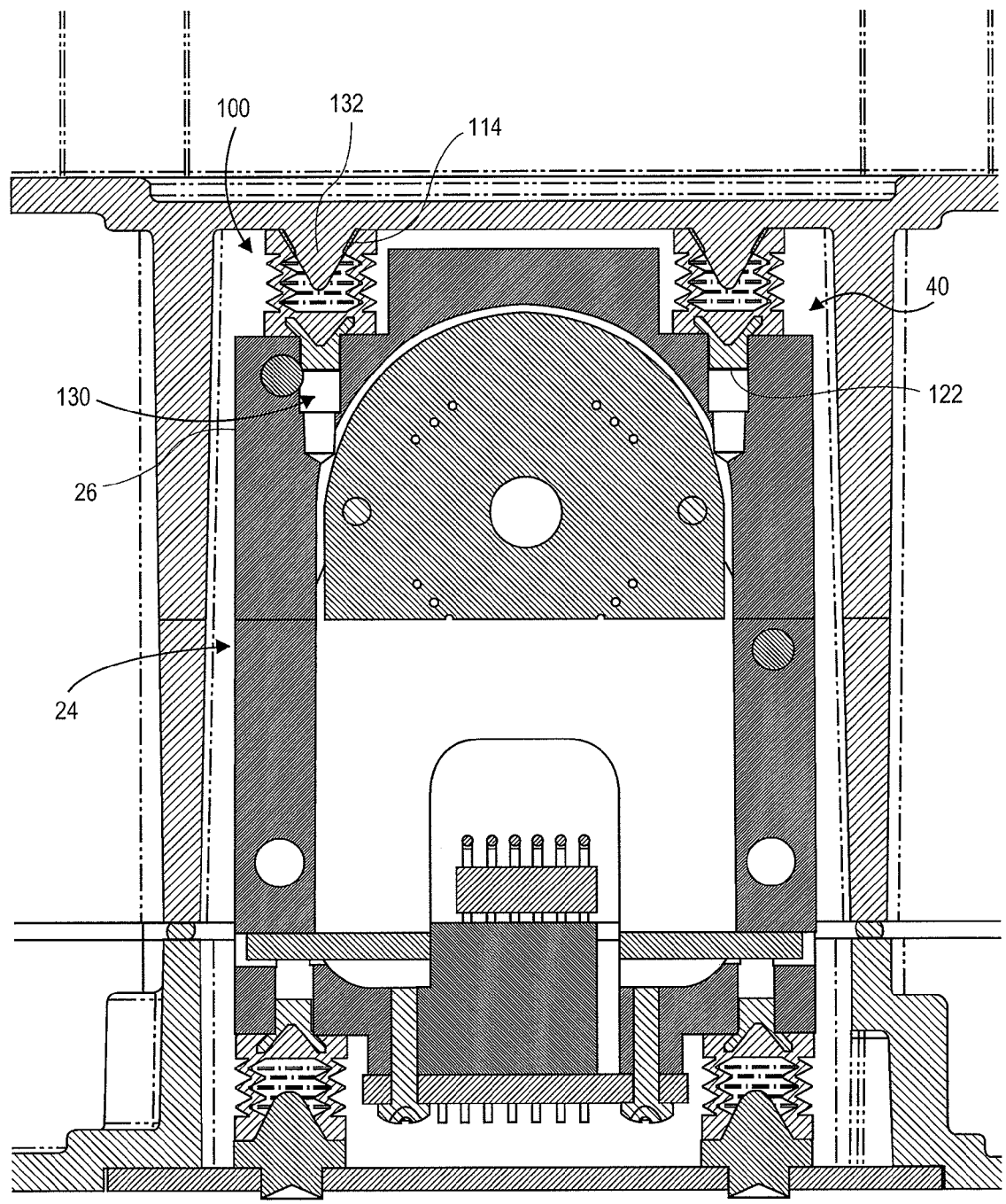
FIG. 5 is a cross-sectional view of the mechanical ventilator illustrated in FIG. 1 showing the inter-relationship of the flexible mounts with the Roots blower housing and a compartment of a mechanical ventilator.

In one embodiment, a resilient mount 100 is located at each of the four corners of the blower housing 26 at its top 36, and at each of its four corners at its bottom 38. In one embodiment, the resilient mounts 100 are connected to the blower housing 26. In one embodiment, as best illustrated in FIG. 5, recesses or openings 130 are provided in the housing 26 for accepting the base 122 of the resilient mounts 100.

In the embodiment illustrated in FIGS. 1 and 2, the compartment 40 is partially defined by one or more wall elements. The wall elements are located in close proximity to the ends 28,30, sides 32,34 and top and bottom 36,38 of the blower housing 26. In one embodiment, openings (not shown) are provided in the walls of the compartment 40 in alignment with the inlet and outlet, respectively, of the compressor 24. The proximal location of the compartment 40 walls to the inlet and outlet of the compressor 24 allows gas to flow through those walls into and out of the compressor 24.

In one embodiment, the spacing between the walls defining the compartment 40 and the ends 28,30 and sides 32,34 of the blower housing 26 are on the order of about 0.04 to 0.06 inches.

The walls that define a top and bottom of the compartment 40 are in one embodiment spaced from the blower housing 26 a sufficient distance to accommodate the resilient mounts 100. In one embodiment, this distance is about 0.04 to 0.10 in.

In one embodiment, the walls that define the top and bottom of the compartment 40 are configured to positively engage the mounts 100. In the embodiment of FIG. 5, projections 132 extend from the walls and engage the tapered openings 114 of the resilient mounts 100. In one embodiment, the projections 132 are conical in shape, having a sloping outer surface that matches that of the tapered opening 114 of the second support portion 112 of the damping member 104. In this configuration, the damping member 104 is configured to engage the projection 132, securing the resilient mount 100 in position.

It will be appreciated that a greater or lesser number of resilient mounts 100 may be used, and their location may vary. For example, resilient mounts 100 may be located at the ends and/or sides of the compressor housing 26 in addition to or instead of at the top and bottom of the blower housing 26.

The various embodiments of the invention have particular advantages. While embodiments of the invention may be used in a variety of environments for reducing or attenuating noise, they have particular applicability to an environment where space is limited, such as in a portable ventilator housing.

It will be understood that the above described embodiments of the method and apparatus of the invention are merely illustrative of applications of the principles of this invention and many other embodiments and modifications may be made without departing from the spirit and scope of the invention as defined in the claims.

What is claimed is:

1. A noise attenuating system disposed in an enclosure of a ventilation system, comprising:

a flow path comprising a plurality of interconnected chambers configured so as to create a plurality of impedance mismatches along said flow path;

a perforated tube disposed in one of said chambers, said perforated tube comprising an inner chamber comprising a wall and a plurality of passages traversing said wall, each of said plurality of passages comprising a tube having a first end and a second end, said first end being disposed at said interior chamber, said second end extending beyond an external dimension of said wall, wherein a length of a flow path along a passage is greater than a thickness of said wall of the ventilation system;

a compressor in fluid communication with said flow path, wherein said noise attenuating system is configured to attenuate noise generated by said compressor; and a mounting system to mount said compressor in said enclosure, said mounting system comprising a plurality of resilient mounts, said mounting system reducing a natural frequency of said compressor when mounted to said resilient mounts from a natural frequency of said compressor when unmounted.

2. The noise attenuating system of claim 1 wherein at least one of said chambers is disposed in an inlet gas flow path from an inlet to said enclosure to an inlet to said compressor.

3. The noise attenuating system of claim 1 wherein at least one of said chambers is disposed in an outlet gas flow path from an outlet of said compressor to an outlet from said enclosure.

4. The noise attenuating system of claim 3 wherein at least one of said chambers is disposed in an inlet gas flow path from an inlet to said enclosure to an inlet to said compressor.

5. The noise attenuating system of claim 1 wherein a plurality of said chambers are disposed in an inlet gas flow path from an inlet to said enclosure to an inlet to said compressor.

6. The noise attenuating system of claim 1 wherein a plurality of said chambers are disposed in an outlet gas flow path from an outlet of said compressor to an outlet from said housing.

7. The noise attenuating system of claim 6 wherein a plurality of said chambers are disposed in an inlet gas flow path from an inlet to said enclosure to an inlet to said compressor.

8. The noise attenuating system of claim 1 wherein at least of one said chambers comprises at least one wall integrally formed with a portion of said enclosure.

9. The noise attenuating system of claim 1 wherein a plurality of said perforated tubes disposed in at least one of said chambers.

10. The noise attenuating system of claim 1 wherein said passages are formed in exterior tubes that project form an exterior surface of said perforated tube.

11. The noise attenuating system of claim 10 wherein said exterior tubes have a circular cross-section.

12. The noise attenuating system of claim 10 wherein said exterior tubes have a rectangular cross-section.

13. The noise attenuating system of claim 10 wherein a sum of cross-sectional areas of said passages is greater than a cross-sectional area of said chamber.

14. The noise attenuating system of claim 10 wherein said exterior tubes are integrally formed with said wall.

15. The noise attenuating system of claim 14 wherein said wall has an original thickness and wherein said exterior tubes are formed by reducing said wall thickness at locations other than the locations at which said exterior tubes are located.

16. The noise attenuating system of claim 10 wherein a first plurality of said exterior tubes have a first length and a second plurality of said exterior tubes have a second length.

17. The noise attenuating system of claim 1 wherein said inner chamber has a circular cross-section.

18. The noise attenuating system of claim of 1 wherein said inner chamber has a rectangular cross-section.

19. The noise attenuating system of claim 11 wherein each of said resilient mounts comprises:
   a support member for supporting said resilient mount relative to said compressor;
   a resilient damping member connected to said support member;
   an opening for receiving a mounting point of a supporting structure;
   said mounting system reducing a natural frequency of said compressor when mounted to said resilient mounts from a natural frequency of said compressor when unmounted.

20. The noise attenuating system of claim 19 wherein said support member comprises a threaded fastener.

21. The noise attenuating system of claim 19 wherein said opening comprises a tapered opening formed in said resilient damping member.

22. The noise attenuating system of claim 19 wherein a first plurality of said resilient mounts are disposed between a first side of said compressor and a first supporting structure and a second plurality of said resilient mounts are disposed between a second side of said compressor and a second supporting structure.

23. The noise attenuating system of claim 22 wherein said first and second supporting structures comprise portions of said ventilator enclosure.

24. The noise attenuating system of claim 19 wherein said resilient damping member comprising a foldable wall portion.

25. The noise attenuating system of claim 24 wherein said foldable wall portion comprises a bellows shaped section.

26. The system of claim 1, wherein the plurality of interconnected chambers configured so as to create the plurality of impedance mismatches along said flow path through chambers include sizing adjacent chambers where they have a cross-sectional flow area substantially larger than the cross sectional area of the flow tube that interconnects the two chambers.

* * * * *